United States Patent
Kulak et al.

(10) Patent No.: US 11,753,437 B2
(45) Date of Patent: Sep. 12, 2023

(54) PEPTIDE PURIFICATION USING MIXED-PHASE SOLID PHASE EXTRACTION MATERIAL

(71) Applicant: MAX-PLANCK-GESELLSCHAFT ZUR FÖRDERUNG DER WISSENSCHAFTEN E.V., Munich (DE)

(72) Inventors: Nils A. Kulak, Munich (DE); Garwin Pichler, Munich (DE); Matthias Mann, Stockdorf (DE)

(73) Assignee: MAX-PLANCK-GESELLSCHAFT ZUR FORDERUNG DER WISSENSCHAFTEN E.V., Munich (DE)

(*) Notice: Subject to any disclaimer, the term of this patent is extended or adjusted under 35 U.S.C. 154(b) by 537 days.

(21) Appl. No.: 15/741,804

(22) PCT Filed: Jul. 8, 2016

(86) PCT No.: PCT/EP2016/066263
§ 371 (c)(1),
(2) Date: Jan. 4, 2018

(87) PCT Pub. No.: WO2017/005898
PCT Pub. Date: Jan. 12, 2017

(65) Prior Publication Data
US 2018/0201644 A1      Jul. 19, 2018

(30) Foreign Application Priority Data
Jul. 9, 2015  (EP) .................................... 15176142

(51) Int. Cl.
*C07K 1/16* (2006.01)
*G01N 33/50* (2006.01)

(52) U.S. Cl.
CPC .......... *C07K 1/165* (2013.01); *G01N 33/5002* (2013.01)

(58) Field of Classification Search
None
See application file for complete search history.

(56) References Cited

FOREIGN PATENT DOCUMENTS

WO       2014/200346 A1     12/2014

OTHER PUBLICATIONS

Keller et al., Interferences and contaminants encountered in modern mass spectrometry, Analytica Chimica Acta, 2008, pp. 71-81, vol. 627.

(Continued)

*Primary Examiner* — Kara M Peo
(74) *Attorney, Agent, or Firm* — Pillsbury Winthrop Shaw Pittman LLP

(57) ABSTRACT

The present invention relates to a method of purifying peptides and/or polypeptides, said method comprising or consisting of: (a) loading a sample comprising peptides and/or polypeptides under acidic or neutral aqueous conditions on mixed-phase solid phase extraction (SPE) material, wherein said material consists of or comprises reversed phase/ion exchange material; (b) washing said mixed-phase SPE material with (ba) an acidic or neutral composition comprising at least 50% (v/v) organic solvent; and/or (bb) an acidic or neutral aqueous solution; and (c) eluting said peptides and/or polypeptides from said mixed-phase SPE material with an alkaline composition comprising at least 50% (v/v) organic solvent.

8 Claims, 1 Drawing Sheet

(56) References Cited

OTHER PUBLICATIONS

Kulak et al., Minimal, encapsulated proteomic-sample processing applied to copy-number estimation in eukaryotic cells, Nature Methods, Mar. 2014, pp. 319-326, vol. 11 No. 3.
McDonald et al., Bioactive Contaminants Leach from Disposable Laboratory Plasticware, Science, Nov. 7, 2008, pp. 917, vol. 322.
Ting et al., MS3 eliminates ratio distortion in isobaric multiplexed quantitative proteomics, Nature Methods, Nov. 2011, pp. 937-942, vol. 8 No 11.
Watson et al., Extraction, Identification, and Functional characterization of a Bioactive Substance from Automated Compound-Handling Plastic Tips, Journal of Biomolecular Screening, 2009, pp. 566-572, vol. 14 No. 5.
European Office Action, Office Action issued in EP Application No. 16738402.3, dated Dec. 2, 2019, pp. 1-8.
Anonymous, Empore High Performance Extraction Disk Cartridges, Oct. 1, 1998, pp. 1-10.
Rappsilber et al., Protocol for micro-purification, enrichment, prefractionation and storage of peptides for proteomics using StageTips, Nature Protocols, Aug. 1, 2007 pp. 1896-1906, vol. 2, No. 8.
Borner et al., Using In-Solution Digestion, Peptide Fractionation, and a Q Exactive Mass Spectrometer to Analyze the Proteome of Clathrin-Coated Vesicles, Cold Spring Harbor Protocol, Nov. 3, 2014, pp. 1192-1201.
Extended European Search Report EP Application No. 15176142.6 dated Jan. 19, 2016.
Written Opinion of the International Searching Authority PCT/EP2016/066263 dated Sep. 13, 2016.
International Search Report PCT/EP2016/066263 dated Sep. 13, 2016.
Jonathan P. Danaceau et al., "Removal of Polyethylene Glycol 400 (PEG 400) from Plasma Samples Using Mixed-Mode Solid-Phase Extraction (SPE)", Oct. 22, 2012, 1 pg., XP55235711, Retrieved from the Internet: URL:http://www.waters.com/webassets/cms/library/docs/2012asms_danaceau_excipient.pdf.
Jonathan P. Danaceau et al."Removal of Polyethylene Glycol 400 (PEG 400) from Plasma Samples Using Mixed-Mode Solid-Phase Extraction", Application Notes, Oct. 1, 2011, pp. 1-7, XP55235703, Retrieved from the Internet: URL:http://www.waters.com/webassets/cms/library/docs/720004127en.pdf.
"Oasis mixed-mode ion-exchange cartridges and 96-well plates", Apr. 10, 2014, pp. 1-6, XP55235509, Retrieved from the Internet URL://http://www.waters.com/webassets/cms/support/docs/716001391.pfd.
Gong Choi et al., "Post-pellet-digestion precipitation and solid phase extraction: A practical and efficient workflow to extract surrogate peptides for ultra-high performance liquid chromatography—tandem mass spectrometry bioanalysis of a therapeutic antibody in the low ng/mL range", Journal of Chromatography vol. 1424, Oct. 19, 2015, pp. 27-36.
European Patent Office, Office Action issued in EP Patent Application No. 16738402.3, dated Oct. 1, 2020, pp. 1-5.
China National Intellectual Property Administration, Chinese Office Action issued in 201680040589.5, dated Jan. 7, 2021, pp. 1-9.
European Patent Office, European Search Report issued in EP Application No. 21151333, dated Apr. 15, 2021, pp. 1-8.
Gong et al., "Post-pellet-digestion precipitation and solid phase extraction: A practical and efficient workflow to extract surrogate peptides for ultra-high performance liquid chromatography—tandem mass spectrometry bioanalysis of a therapeutic antibody in the low ng/mL range", Journal of Chromatography A, Oct. 19, 2015, pp. 27-36, vol. 1424.
"Oasis mixed-mode ion-exchange cartridges and 96-well plates", retrieved from the Internet: URL:http://www.waters.com/webassets/cms/support/docs/716001391.pdf, Apr. 10, 2014, pp. 1-6.
Danaceau et al., "Removal of Polyethylene Glycol 400 (PEG 400) from Plasma Samples Using Mixed-Mode Solid-Phase Extraction", Retrieved from the Internet: URL:http://www.waters.com/webassets/cms/library/docs/720004127en.pdf, Oct. 1, 2011, pp. 1-7.
Danaceau et al., "Removal of Polyethylene Glycol 400 (PEG 400) from Plasma Samples Using Mixed-Mode Solid-Phase Extraction (SPE)", Retrieved from the Internet: URL:http://www.waters.com/webassets/cms/library/docs/2012asms danaceau excipient.pdf, Oct. 22, 2012, pp. 1-1.
Australian Government, Official Action issued in AU Patent Application No. 2016290650, dated Aug. 9, 2021, pp. 1-4.
China National Intellectual Property Administration, Second Office Action issued in CN Patent Application No. 201680040589.5, dated Jul. 22, 2021, pp. 1-6.
Canadian Intellectual Property Office, Official Action issued in Canadian Patent Application No. 2,989,261, dated May 19, 2021, pp. 1-5.

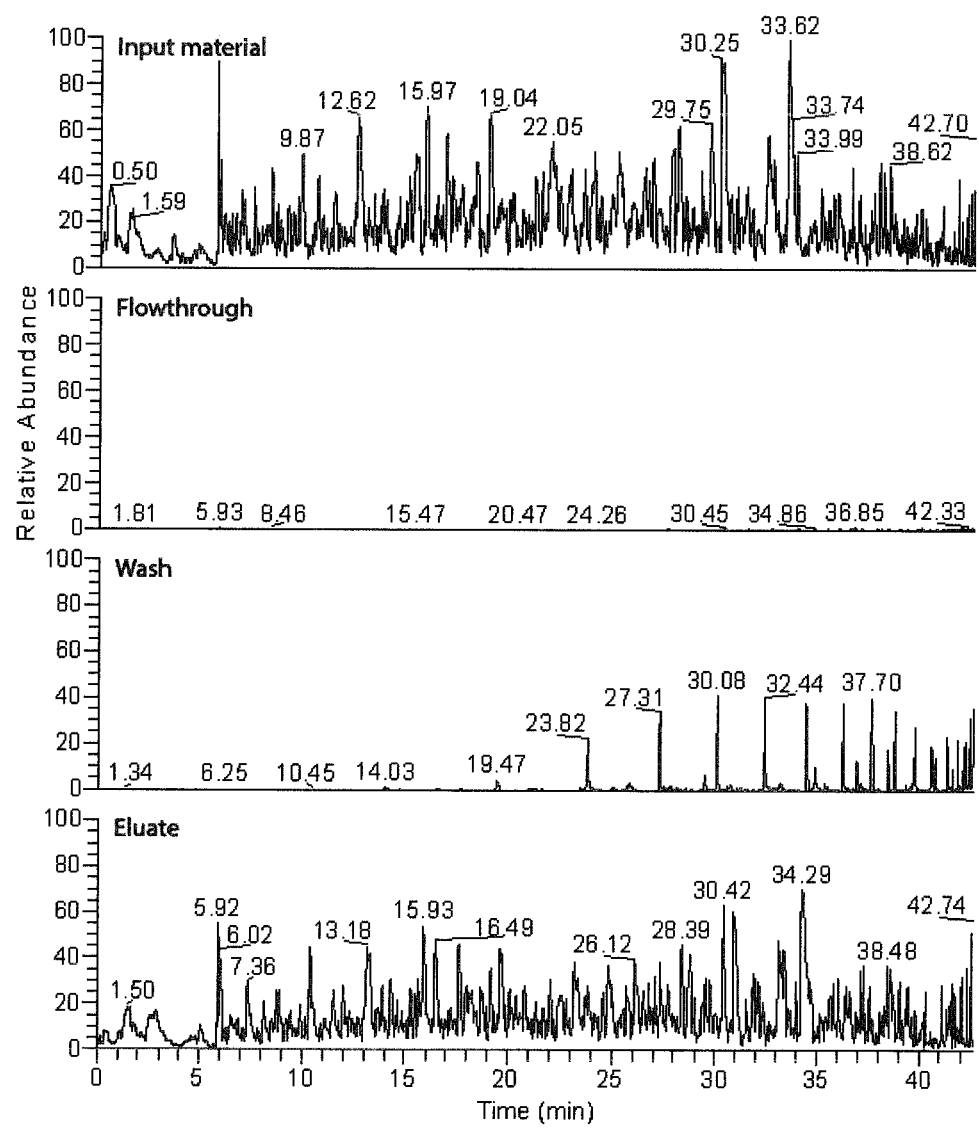

PEPTIDE PURIFICATION USING MIXED-PHASE SOLID PHASE EXTRACTION MATERIAL

CROSS-REFERENCE TO RELATED APPLICATIONS

This application is the U.S. National Phase of International Application No. PCT/EP2016/066263, filed Jul. 8, 2016, which claims priority to European Patent Application No. 15176142.6, filed Jul. 9, 2015. The subject matter of each of these applications is incorporated herein by reference in their entirety.

The present invention relates to a method of purifying peptides and/or polypeptides, said method comprising or consisting of: (a) loading a sample comprising peptides and/or polypeptides under acidic or neutral aqueous conditions on mixed-phase solid phase extraction (SPE) material, wherein said material consists of or comprises reversed phase/ion exchange material; (b) washing said mixed-phase SPE material with (ba) an acidic or neutral composition comprising at least 50% (v/v) organic solvent; and/or (bb) an acidic or neutral aqueous solution; and (c) eluting said peptides and/or polypeptides from said mixed-phase SPE material with an alkaline composition comprising at least 50% (v/v) organic solvent.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

State-of-the art bottom-up proteomics platforms often comprise highly sensitive components such as nano-flow high-pressure liquid-chromatography (nano HPLC) systems, an electrospray ionization (ESI) source, and a mass-spectrometer (MS) containing a selection quadrupole. Any contamination of these components can lead to the loss of valuable sample, decrease in system performance and entire system failures with time consuming instrument downtimes and extended repairs.

Contaminating compounds can originate from the sample itself or the materials used for sample preparation. Especially clinically relevant tissues and bodily fluids contain undesirable substances such as high contents of salts, fats, lipids, and sugars which harm chromatography and electrospray quality. Furthermore, plastics and chemical components which are used during sample handling may introduce interfering ions which influence LC-MS measurements. Especially LC-MS incompatible detergents can be very destructive by either damaging chromatography media or flooding the instrument and covering peptide ions during measurements.

Interfering ions are commonly observed in mass spectrometry often referred to as background ions. These ions are often present in laboratory air but the most abundant and chromatographically resolved contaminating ions are typically present in the sample which is analyzed. As noted above, these originate from chemicals or plastics employed during sample handling (Keller, B. O., et al., Interferences and contaminants encountered in modern mass spectrometry, Anal Chim Acta, 2008. 627(1): p. 71-81; McDonald, G. R., et al., Bioactive contaminants leach from disposable laboratory plasticware, Science, 2008. 322(5903): p. 914; Watson, J., et al., Extraction, identification, and functional characterization of a bioactive substance from automated compound-handling plastic tips. J Biomol Screen, 2009. 14(5): p. 566-72). These oligomers or polymers are typically in a similar mass range as peptides and may behave similarly in LC-MS measurements. Furthermore, chemical labeling often leads to side-products which can be very pronounced in LC-MS measurements (Ting, L., et al., MS3 eliminates ratio distortion in isobaric multiplexed quantitative proteomics. Nat Methods, 2011. 8(11): p. 934-40). When samples are pooled or combined as in isotope labeling approaches, the presence of these polymers is further pronounced due to additive effects while sample specific analytes are diluted down resulting in poor measurement quality.

Interfering ions can flood the mass spectrometer and thereby cover the analytes of interest. Such contaminants are mostly reduced using specialized plastic ware, chemicals of outstanding purity, or are reduced by time consuming protein precipitation steps. Precipitation at peptide level is not advisable, though, because small polypeptides tend not to precipitate and therefore precipitation would lead to severe sample loss.

The main alternatives to precipitation are chromatographic means of binding, washing, and elution. While SPE materials have been previously reported for desalting and detergent removal purposes, they were not designed and optimized for removal of the contaminants discussed above.

Many biological samples of high interest contain large quantities of LC-MS contaminating compounds. Especially clinically relevant samples such as blood plasma, serum, and urine samples are difficult to analyze due to a large content of lipids, salts, sugars, and other metabolites (Table 1). These contaminating agents often cause clogging of LC columns and decreased performance of the mass spectrometer. This is partially the reason why large-scale LC-MS studies of these body fluids were either unsuccessful or are extremely challenging.

TABLE 1

Protein, lipid, sugar, and salt in dry mass in plasma and urine.

| Type | Plasma (dry mass) | Urine (dry mass) |
| --- | --- | --- |
| Protein | ~92.6% | ~0.5% |
| Lipids | ~5.8% | ~0.0% |
| Sugars | ~1.3% | ~13.2% |
| Salts | ~0.2% | ~86.3% |

Finally, certain enrichment protocols even lead to increased content of contaminants. Sucrose gradients introduce large amounts of sugars and membrane enrichment protocols lead to increased concentrations of lipids and fatty acids.

In view of the deficiencies of the prior art, the technical problem underlying the present invention can be seen in the provision of alternative or improved methods of purifying peptides and/or polypeptides.

In a first aspect, the present invention provides a method of purifying peptides and/or polypeptides, said method comprising or consisting of: (a) loading a sample comprising peptides and/or polypeptides under acidic or neutral aqueous conditions on mixed-phase solid phase extraction (SPE) material, wherein said material consists of or comprises reversed phase/ion exchange material; (b) washing said mixed-phase SPE material with (ba) an acidic or neutral composition comprising at least 50% (v/v) organic solvent;

and/or (bb) an acidic or neutral aqueous solution; and (c) eluting said peptides and/or polypeptides from said mixed-phase SPE material with an alkaline composition comprising at least 50% (v/v) organic solvent.

The term "purifying" as used herein has its art-established meaning. It refers to the preparation of an analyte, in this case a peptide or polypeptide, in pure or substantially pure form. Purifying is the removal of contaminants. Contaminants may be of biological or chemical origin. Generally, a biological contaminant is a contaminant which originates from the sample. A chemical contaminant generally is a contaminant which is introduced during sample handling. The present invention provides for the removal of both biological and chemical contaminants. In terms of physicochemical properties, the present invention provides for the removal of both hydrophobic, hydrophilic and amphipathic contaminants. Typically or preferred contaminants to be removed are further detailed below. The pure form of the analyte may be solid or liquid, liquids including solutions of the analytes. It goes without saying that removal of solvent, water or of buffered aqueous solution is not a requirement for purity. In fact, it is well-known in the art that peptide and polypeptide solutions should generally be buffered. Preferred buffer substances in that respect include, but are not limited to acetic acid, formic acid, trifluoroacetic acid, ammonium acetate, and ammonium formate.

For the purposes of the present invention, a preparation of peptides or polypeptides is considered pure or essentially pure if non-peptide and non-polypeptide compounds have (essentially) been removed. The methods of the present invention do not aim at separating peptides or polypeptides from each other. Typical contaminants which the present methods are capable of removing from a sample are described in the background section herein above and are the subject of a preferred embodiment disclosed further below.

In terms of degrees of purity, the methods of the present invention provide purified peptides and polypeptides at a level of at least 60%, at least 70%, more preferably at least 80%, at least 90%, at least 91%, at least 92%, at least 93%, at least 94%, at least 95%, at least 96%, at least 97%, at least 98%, or at least 99% purity. Preferred is also that peptides or polypeptides are the only analytes above the detection level. Preferred means of detection are mass spectrometry and UV/vis spectroscopy.

To the extent the methods of the present invention yield solid purified products, the above disclosed percentage values are weight/weight percentages (% (w/w)). To the extent the methods of the invention yield liquid compositions comprising purified peptides or polypeptides, the above disclosed percentage values refer to weight/weight percentages of lyophilisates obtainable from said liquid compositions.

Owing to the presence of one or more charges or potentially charged groups such as N-terminus, C-terminus and side chains, it is generally required for a peptide or a polypeptide molecule to be electrostatically neutral that one or more cations and/or one or more anions are associated with said peptide or polypeptide. Such cations and anions are not viewed as contaminants in accordance with the present invention. Preferred cations in that respect are alkaline metal ions, alkaline earth metal ions and ammonium. Preferred anions include halogenides, sulfate, phosphates and acetate.

The terms "peptide" and "polypeptide", respectively, have their art-established meaning. Either one is a polycondensate of amino acids, wherein peptides consist of up to and including 30 amino acids, and polypeptides of more than 30 amino acids. In typical applications of the methods of the present invention, said peptides or polypeptides are the result of a tryptic digest of a sample of biological origin and comprising proteins and polypeptides. A preferred length range for the peptides and polypeptides is from 4 to 50 amino acids. To the extent longer polypeptides are to be purified, the preferred upper length limit is about 500 amino acids.

The monomeric building blocks of peptides and polypeptides are preferably the 20 standard $\alpha$-amino acids. Having said that, other naturally occurring or non-naturally occurring amino acids are deliberately envisaged as building blocks. Examples thereof are selenomethonine, pyrrolysine and hydroyproline. Ornitine and canavanine are further atypical amino acids.

Generally, preference is given to $\alpha$-amino acids as monomer building blocks of peptides and polypeptides in accordance with the present invention. This, however, does not exclude other positions for the amino group such as in $\beta$-amino acids or $\gamma$-amino acids.

Peptides and polypeptides may contain post-translational modifications such as phosphorylation, glycation, glycosylation and methylation. These and other post-translational modifications are well-known in the art as are the typical attachment sites in peptides, polypeptides and proteins.

In terms of the functional group connecting two monomeric units, preference is given to the peptide bond. Optional is the presence of isopeptide bonds or reverse peptide bonds. The backbone may be yet further modified such as it is conventionally done in peptidomimetics. For example, instead of peptide bonds, esters, ethers or alkyl moieties may be present.

Also modifications of the side chains in a backbone of peptide bonds (which optionally may contain also any of the above described alternative backbone functional groups), are envisaged. A particular example are peptide nucleic acids (PNAs).

The term "loading" in connection with the methods of the present invention refers to bringing into contact under conditions that allow binding, more specifically binding of peptides or polypeptides to the SPE material recited above. In typical applications, this is done by pouring a liquid sample onto said material. Peptides and polypeptides bind to said SPE material, interactions typically including hydrophobic and ionic interactions.

As noted further below, preference is given to performing one, more or all steps of loading, washing and eluting in accordance with the methods of the present invention in columns. A strict requirement does not arise in that respect, though; one, more or all steps may also be performed in batch mode.

The term "sample" in accordance with the present invention is not particularly limited. Samples may be bodily fluids, supernatants of cell cultures, homogenized tissue or broken up cells. Prior to said loading, any of these samples may be subjected to a pre-purifying procedure such as filtration and/or centrifugation.

Preferred bodily fluids in accordance with the present invention are blood, serum, plasma, urine and saliva.

The term "solid phase extraction material" has its art-established meaning. It designates a solid composition of matter which absorbs analytes, typically analytes to be purified. The process of purification, especially when performed in columns, is also known as chromatography. In many instances, the term "matrix" is used with a meaning equivalent to that of "material". According to the present invention, the solid phase extraction material to be used for the methods disclosed herein is mixed-phase solid phase extraction material. The term "mixed-phase" designates material which exhibits two distinct physicochemical properties. Such physicochemical properties are relevant for the absorption of analytes. In accordance with the invention, "mixed-phase" designates the concomitant presence of reversed phase material and ion exchange material. By choosing appropriate functional groups, a single material may implement both purification capabilities. Preferred mixed-phase SPE material is disclosed further below.

The terms "acidic" and "neutral" designate pH-values below 7 and of 7, respectively.

The term "aqueous conditions" in conjunction with the loading step refers to the sample comprising peptides and/or polypeptides being an aqueous composition. Preferably, the term "aqueous conditions" extends to said SPE material, or, in the corresponding preferred embodiment, the column comprising said SPE material, being equilibrated or preconditioned with an aqueous composition.

Aqueous conditions do not imply a requirement for an organic solvent. The absence of any organic solvent is preferred. Having said that, organic solvent may be present, wherein preferred organic solvents are disclosed herein below. For conditions to be aqueous, the percentage of organic solvent is below 50% (v/v), below 40% (v/v), below 30% (v/v), below 20% (v/v), below 10% (v/v), below 5% (v/v), below 2% (v/v), below 1% (v/v), or below 0.1% (v/v).

Preferred pH-values as well as preferred means of acidifying are disclosed further below.

Loading under acidic conditions is preferred over loading under neutral conditions.

Washing in accordance with step (b) of the first aspect of the present invention serves to remove contaminants, while the analytes of interest, namely peptides and polypeptides, remain bound to the SPE material. In accordance with the present invention, two wash steps designated (ba) and (bb) herein above are provided. In its broadest form, the invention extends to embodiments where only washing in accordance with (ba) or only washing in accordance with (bb) is performed. Preferably, though, both washing steps, namely in accordance with (ba) and (bb), are performed.

The washing solution in accordance with (ba) is an acidic or neutral composition comprising at least 50% (v/v) organic solvent, preferred organic solvents being defined further below. Also higher contents of organic solvent such as at least 60% (v/v), at least 70% (v/v), at least 80% (v/v), at least 90% (v/v), at least 95% (v/v), at least 97% (v/v), at least 98% (v/v), at least 99% (v/v) or 100% (v/v) are deliberately envisaged. At least 90% (v/v) is a particularly preferred value. In principle, there is no upper limit, 100% (v/v) being also especially preferred, even though, in practical terms a minimal water contents of about 0.1% (v/v) may be present.

Noting that eluting in accordance with step (c) also makes use of a composition comprising organic solvent, we note that it is possible but not preferred to use the same organic solvent for washing and eluting. As such, the organic solvent used for washing may also be designated "first organic solvent", and the organic solvent to be used for eluting may also be designated "second organic solvent".

Generally speaking, acidic compositions or solutions, respectively, are preferred over the neutral counterparts for the purpose of washing.

The washing solution in accordance with (ba) may consist of said organic solvent, water, and, to the extent it is acidic, means for acidifying, and optionally a salt. 100% (v/v) alcohol, preferred alcohols being disclosed below, is especially preferred.

The washing solution in accordance with (bb) may consist of water and, to the extent the solution is acidic, means for acidifying, and optionally a salt. A 0.2% (v/v) trifluoroacetic acid solution is preferred.

As noted above, washing may be performed in columns or in batch format. This applies independently to both steps (ba) and (bb).

The term "organic solvent" refers to an organic compound which is liquid at room temperature. An organic solvent in accordance with the invention preferably has a dielectric constant at 20° C. which is below 50, preferably below 25. Exemplary and preferred organic solvents are disclosed further below.

Eluting in accordance with the methods of the present invention involves a change in conditions such that said peptides and polypeptides which have bound to the SPE material during loading and remained bound during washing are removed from said material. The eluent to be used is an alkaline composition comprising at least 50% (v/v) organic solvent. Also higher contents of organic solvent such as at least 60% (v/v), at least 70% (v/v), at least 80% (v/v), at least 90% (v/v), at least 95% (v/v), at least 97% (v/v), at least 98% (v/v), at least 99% (v/v) or 100% (v/v) are deliberately envisaged.

The term "alkaline" refers to a pH greater than 7. Preferred alkaline pH ranges as well as preferred means of rendering alkaline are disclosed further below. As noted above, the organic solvent comprised in the eluent may also be designated "second organic solvent".

A preferred eluent according to (c) is 80% (v/v) ACN and 5% (v/v) ammonia in water.

Wash step (ba) solubilizes and removes from the SPE material hydrophobic and weakly cationic compounds. These compounds include, for example, lipids and plasticizers as well as oligomeric or polymeric material from the walls of vessels used for sample handling. Peptides and polypeptides remain bound owing to their strong interactions with the ion exchange component in said mixed phase SPE material. Washing in accordance with step (bb) leads to the solubilization of salts and substances without or a low degree of hydrophobic surfaces.

Peptides and polypeptides remain bound also under conditions in accordance with step (bb) owing to their hydrophobic interaction with mixed phase SPE material. As such, hydrophilic contaminants are removed in step (bb). Elution of peptides occurs only in step (c) which involves a combination of the use of organic solvents with alkaline conditions.

Depending on the type of contaminants present in the sample or expected to be present, any appropriate choice of the washing steps can be made. In case the nature of the contaminants is unknown, use of both washing steps (ba) and (bb) is recommended.

The methods of the present invention provide for an excellent removal of contaminants, which contaminants may vary greatly in terms of physicochemical properties. Use of the method of purifying in accordance with the present invention provides for improved performance and lower risk of failure in all downstream processes. Preferred downstream processes include analysis by means of mass spectrometry or UV/vis spectroscopy. Liquid chromatography combined with mass spectrometry (LC-MS) is a particular preferred embodiment of the conceivable downstream processing steps. Both liquid chromatography as well as analysis in the mass spectrometer are significantly improved owing to the higher degree of purity of the compositions comprising peptides and/or polypeptides as obtained by the methods of the present invention when compared to established procedures.

In a second aspect, the present invention provides a method of purifying peptides and/or polypeptides bound to mixed-phase SPE material, said method comprising or consisting of: (a) washing said mixed-phase SPE material with (aa) an acidic or neutral composition comprising at least 50% (v/v) organic solvent; and/or (ab) an acidic or neutral aqueous solution; and (b) eluting the peptides and/or polypeptides from said mixed-phase SPE material with an alkaline composition comprising at least 50% (v/v) organic solvent.

Any definitions, explanations and preferred embodiments (as disclosed below and above) apply mutatis mutandis to both the first and the second aspect of the present invention.

In a preferred embodiment of the methods of the first and the second aspect, said mixed-phase SPE material is sulfonated poly-divinyl benzene (DVB) or sulfonated polystyrene divinyl benzene (SDB). Manufacturers and their commercially available products include Generik BCX of Sepax Technologies (Newark, Del., US) and SDB-RPS of 3M (e.g. 3M Germany, Neuss). A further manufacturer is Dr. Maisch (Germany).

Sulfonation introduces functional groups which renders the otherwise hydrophobic material capable of performing as an ion exchange material in addition to its capabilities as reversed phase material.

In preferred embodiments, the loading conditions have a pH greater or equal 1 and less than 7, preferably a pH between 3 and 4.

In further preferred embodiments, said acidic organic solvent has a pH greater or equal 1 and less than 7, preferably a pH between 3 and 4.

In further preferred embodiments, said acidic aqueous solution has a pH greater or equal 1 and less than 7, preferably a pH between 3 and 4.

In either case, preferred acids to be used for acidifying are acids compatible with a downstream use of the purified peptides and polypeptides in mass spectrometry. In structural terms, suitable acids are formic acid (FA), acetic acid and trifluoroacetic acid (TFA).

In a further preferred embodiment, said alkaline organic solvent has a pH greater than 7 and less or equal 14, preferably a pH between 8 and 10.

Similar to the considerations in relation to acids, it is preferred to use bases which are compatible with downstream analysis of the purified peptides and polypeptides in a mass spectrometer. Also, preference is given to volatile bases. Examples meeting either requirement are ammonia, triethylammonia (TEA), ammonium formate (AF), and ammonium acetate.

In a further preferred embodiment of any of the preceding embodiments, be it the first or second aspect or any preferred embodiment thereof, the organic solvent for washing and the organic solvent for eluting are independently chosen from (a) alcohols, preferably primary or secondary unbranched, branched or cyclic $C_1$ to $C_6$ alkanoles such as methanol, ethanol, 2-propanol or butanol; (b) alkanes, preferably unbranched, branched or cyclic $C_5$ to $C_{10}$ alkanes such as hexane, cyclohexane, pentane or isopentane; (c) halogenated hydrocarbons, preferably chlorinated hydrocarbons such as chlorinated unsubstituted or substituted $C_1$ to $C_6$ unbranched, branched or cyclic alkanes, including chloroform and dichloromethane, or fluorinated hydrocarbons such as fluorinated unsubstituted or substituted $C_1$ to $C_6$ unbranched, branched or cyclic alkanes, including trifluoroethanol, substituents preferably being one or two hydroxy groups; (d) ethers, preferably linear or cyclic ethers with 3 to 10 carbon atoms and 1 to 3 ether oxygen atoms such as diethyl ether, tetrahydrofuran, ethyl methyl ether or 1,4-dioxane; (e) ketones, preferably linear or cyclic ketones with 2 to 10 carbon atoms, such as acetone; (f) nitriles, preferably primary or secondary unbranched, branched or cyclic $C_1$ to $C_6$ nitriles such as acetonitrile (abbreviated as "ACN"); (g) sulfoxides, preferably dialkyl sulfoxides, alkyl being unbranched, branched or cyclic $C_1$ to $C_6$ alkyl, such as DMSO; and (h) esters, preferably esters of unbranched, branched or cyclic $C_1$ to $C_6$ alkanoic acids with unbranched, branched or cyclic $C_1$ to $C_6$ alkanoles; such as ethyl acetate.

Dielectric constants of specific solvents according to the invention are given in Table 2 below.

TABLE 2

Dielectric constants at room temperature of specific solvents.

| Solvent | Dielectric constant |
| --- | --- |
| Methanol | 33 |
| Ethanol | 24.55 |
| 2-propanol | 18 |
| Butanol | 18 |
| Hexane | 1.88 |
| Cyclohexane | 2.02 |
| Pentane | 1.84 |
| Isopentane | 1.8 |
| Chloroform | 4.81 |
| Dichloromethane | 9.1 |
| Trifluoroethanol | 26.67 |
| Diethyl ether | 4.33 |
| tetrahydrofuran | 7.6 |
| Ethyl methyl ether | 4.33 |
| 1,4-dioxane | 2.25 |
| Acetone | 20.7 |
| Acetonitrile | 37.5 |
| DMSO | 46.7 |
| Ethyl acetate | 6.02 |

As noted above, said first organic solvent and said second organic solvent may be the same. Preference, though, is given to said first and said second organic solvent being different.

In a particular preferred embodiment, said washing with an acidic or neutral composition comprising at least 50% (v/v) organic solvent is washing with an acidic or neutral composition comprising at least 50% (v/v) alcohol; and/or eluting is with an alkaline composition comprising at least 50% (v/v) acetonitrile. Preferred alcohols are disclosed above. Preferred is 99% (v/v), 99.9% (v/v) or (100% (v/v)) alcohol.

Generally speaking, and in particular in conjunction with the above disclosed particularly preferred embodiment, it is preferred to use an acidic composition comprising said alcohol, the term "acidic" preferably referring to a pH between 3 and 4. The alkaline conditions for eluting are preferably characterized by pH between 8 and 10. Preferably, both washing steps (ba) and (bb) are performed. Preferably, all steps (loading, washing and eluting) are performed in column format.

In a further preferred embodiment, said purifying comprises or consists of the reduction of the amount or the removal of one or more of the following: salts; detergents; lipids; saccharides, especially mono- and disaccharides; polymeric or oligomeric wall material of vessels used for sample handling; and plasticizers. This list of contaminants is not exhaustive. Yet, these are the most frequent contaminants which may severely impact the quality of downstream analysis, downstream analysis preferably being effected in the mass spectrometer. Further information in relation to these contaminants can be found in the background section of the present application. Preferred degrees of purity obtainable by the methods of the invention are disclosed above.

In a further preferred embodiment, one, more or all steps of loading, washing and eluting are effected in columns. Pre-packed columns are available from the above mentioned manufacturers.

In a third aspect, the present invention provides the use of an organic solvent as defined herein above, preferably an alcohol, for washing mixed-phase SPE material under acidic or neutral conditions, said material consisting of or comprising reversed phase/ion exchange material and having peptides bound, and/or of an organic solvent as defined herein above, preferably acetonitrile, for eluting peptides from said mixed-phase SPE material under alkaline conditions.

Any preferred embodiments disclosed herein above in conjunction with methods of the present invention apply mutatis mutandis also to the use in accordance with the third aspect. Preferred are alcohols with a dielectric constant below 25 at room temperature. Preferred is the use of 99.9% (v/v) or 100% (v/v) alcohol.

The use in accordance with the present invention may be the use of a single composition, namely either a composition for washing or a composition for eluting, or it may be a combined use of two compositions, one for washing and one for eluting.

In a further preferred embodiment of the use according to the present invention, any embodiments of said use as disclosed above may be combined with the use of an acidic or neutral aqueous solution for washing mixed phase SPE material, said material being as defined above.

In a fourth aspect, the present invention provides a kit comprising or consisting of (a) mixed-phase SPE material; and (b) one, more or all of (ba) an alcohol; (bb) acetonitrile; and (bc) an acidic or neutral aqueous solution.

A preferred kit in accordance with the present invention comprises or consists of mixed phase SPE material and an alcohol. A further preferred kit comprises or consists of mixed phase SPE material and acetonitrile. A further preferred kit comprises or consists of mixed phase SPE material, an alcohol and acetonitrile.

Preferably, said acidic or neutral aqueous solution, to the extent it is comprised in the kit according to the present invention, is acidic, more preferably it has pH value between 3 and 4.

Preferred alcohols are disclosed herein above. Preferred are alcohols with a dielectric constant below 25 at room temperature.

In a preferred embodiment of the use according to the third aspect and of the kit according to the fourth aspect, said mixed-phase SPE material is sulfonated poly-divinyl benzene (DVB) or sulfonated poly-styrene divinyl benzene (SDB).

In a further preferred embodiment, said kit further comprises (a) means for acidifying said solvent; (b) means for rendering said solvent alkaline; and/or (c) a manual containing instructions for performing the method of the first and the second aspect of the present invention.

Preferred means of acidifying and rendering alkaline, respectively, are disclosed herein above.

The FIGURES show:

FIG. 1: HeLa peptides were spiked with PEG polymers. Washing with 100% alcohol removes polymer contaminants from the sample and thereby improves sample quality and purity.

The Examples illustrate the invention.

EXAMPLE 1

Serum Samples

Using the above disclosed method, 160 patient serum samples could be prepared and analyzed without any interruption or decrease in performance. Among the patient materials were 20 samples of hyperlipidemia, known for their very high lipid content. These samples are typically even harder to handle and cause severe interference in immune-assays.

In more detail, serum samples were collected and diluted 1:10 with double-distilled water. The samples were the digested using the 'iST'-sample preparation method (Kulak, N. A., et al., Minimal, encapsulated proteomic-sample processing applied to copy-number estimation in eukaryotic cells, Nat Methods, 2014 March 11(3) p. 319-24). Peptides were loaded onto a sulfonated styrene-divinylbenzene matrix and washed with 100% alcohol. The matrix was then washed also with a 0.2% (v/v) TFA solution end eluted with 80% (v/v) ACN, 5% (v/v) ammonia. The peptides were measured by nanoLC-MS/MS and analyzed using the MaxQuant environment.

EXAMPLE 2

Urine Samples

The disclosed methods were applied to urine samples which have generally a very high content of salts and metabolites.

Second-morning urine was collected from apparently healthy donors and centrifuged to remove cell debris. The supernatants were concentrated and digested using the 'iST'-sample preparation method (Kulak et al; loc. cit.). Peptides were loaded onto a sulfonated styrene-divinylbenzene matrix and washed with 100% alcohol. The matrix was then washed also with a 0.2% (v/v) TFA solution end eluted with 80% (v/v) ACN, 5% (v/v) ammonia. The peptides were measured by nanoLC-MS/MS and analyzed using the MaxQuant environment.

More than 30 samples could be prepared and analyzed without any interference and with unprecedented quality. The observations demonstrate the effective removal of undesired contaminants also from urine.

EXAMPLE 3

Contaminants Introduced During Processing

As noted above, enriching membrane components generates samples which are particularly challenging.

Vesicles were enriched using a glucose gradient system. Each glucose fraction was then digested using the 'iST'-sample preparation method (Kulak et al; loc. cit.). Peptides were loaded onto a sulfonated styrene-divinylbenzene matrix and washed with 100% alcohol. The matrix was then washed also with a 0.2% (v/v) TFA solution end eluted with 80% (v/v) ACN, 5% (v/v) ammonia. The peptides were measured by nanoLC-MS/MS and analyzed using the MaxQuant environment.

The methods of the present invention allowed the measurement of 160 membrane enrichments on a single nano-flow column as compared to three injections which is what normally is feasible without the methods of the invention.

As such, the disclosed clean-up therefore permits to significantly increase the number of injections.

EXAMPLE 4

Removal of Polymers from HeLa Sample

The disclosed invention relates to the removal of polymers from complex peptide mixtures. The data displayed in FIG. 1 provide evidence that washing in accordance with the invention specifically removes polymers.

The invention claimed is:

1. A method of purifying peptides and/or polypeptides bound to mixed- phase SPE material, said method comprising:
   (a) loading a sample comprising peptides and/or polypeptides under acidic or neutral aqueous conditions on mixed-phase solid phase extraction (SPE) material comprising reversed phase material and/or ion exchange material;
   (b) washing with
      (ba) an acidic composition having a pH from 1 to 4 and comprising at least 50% (v/v) organic solvent; and
      (bb) an acidic or neutral aqueous solution; and
   (c) eluting the peptides and/or polypeptides from said mixed-phase SPE material with an alkaline composition comprising at least 50% (v/v) organic solvent;
   wherein said mixed-phase SPE material is sulfonated poly-divinyl benzene (DVB) or sulfonated poly-styrene divinyl benzene (SDB); and
   wherein step (a) is performed prior to step (b) which is performed prior to step (c).

2. The method of claim 1, wherein the acidic composition in step (ba) has a pH from 3 to 4.

3. The method of claim 1, wherein the acidic aqueous solution in step (bb) has a pH from 3 to 4.

4. The method of claim 1, wherein the alkaline composition in step (c) has a pH from 8 to 10.

5. The method of claim 1, wherein the organic solvent in step (ba) and the organic solvent in step (c) are independently chosen from the group consisting of:
   (a) alcohols;
   (b) alkanes;
   (c) halogenated hydrocarbons;
   (d) ethers;
   (e) ketones;
   (f) nitriles;
   (g) sulfoxides; and
   (h) esters.

6. The method of claim 1, wherein the acidic composition in step (ba) comprises at least 50% (v/v) alcohol; and/or the alkaline composition in step (c) comprises at least 50% (v/v) acetonitrile.

7. The method of claim 1, wherein said purifying comprises the reduction of the amount or the removal of one or more of the following: detergents; lipids;
   saccharides; polymeric or oligomeric wall material of vessels used for sample handling; and
   plasticizers.

8. The method of claim 1, wherein the method is performed using column chromatography.

* * * * *